United States Patent [19]
North, Jr.

[11] Patent Number: 4,989,977
[45] Date of Patent: Feb. 5, 1991

[54] FLOW CYTOMETRY APPARATUS WITH IMPROVED LIGHT BEAM ADJUSTMENT

[75] Inventor: Howard L. North, Jr., Los Gatos, Calif.

[73] Assignee: Becton, Dickinson and Company, Franklin Lakes, N.J.

[21] Appl. No.: 760,205

[22] Filed: Jul. 29, 1985

[51] Int. Cl.[5] .................................... G01N 21/64
[52] U.S. Cl. .................................... 356/338
[58] Field of Search .................. 356/343, 338, 399; 380/484

[56] References Cited

U.S. PATENT DOCUMENTS

| | | | |
|---|---|---|---|
| 3,826,364 | 7/1974 | Bonner et al. | |
| 3,838,912 | 10/1974 | Arimoto et al. | 350/484 |
| 3,941,477 | 3/1976 | Schodl | 356/343 |
| 4,243,318 | 1/1981 | Stöhr | 356/39 |
| 4,293,221 | 10/1981 | Kay et al. | 356/318 |
| 4,577,964 | 3/1986 | Hansen, Jr. | 356/343 |

Primary Examiner—Richard A. Rosenberger
Attorney, Agent, or Firm—Aaron Passman

[57] ABSTRACT

A flow cytometry apparatus for determining one or more characteristics of particles or the like flowing in a liquid stream includes a nozzle for generating a liquid flow stream for moving particles therethrough substantially one at a time. A light source provides a beam of focused light to illuminate the particles moving in the stream. A beam steering member is positioned to adjust the focal point of the light beam on the particles by refracting the light beam to cause a displacement of the focal point. At least one detector is provided for detecting light and for associating that light with one or more characteristics of each particle.

5 Claims, 2 Drawing Sheets

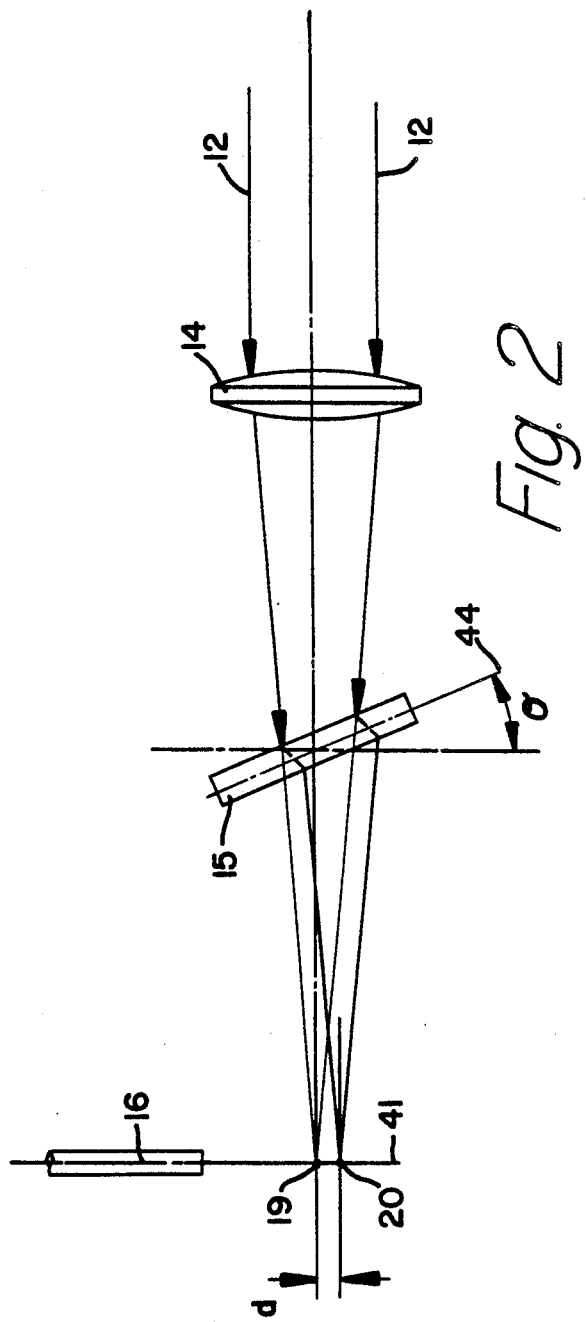
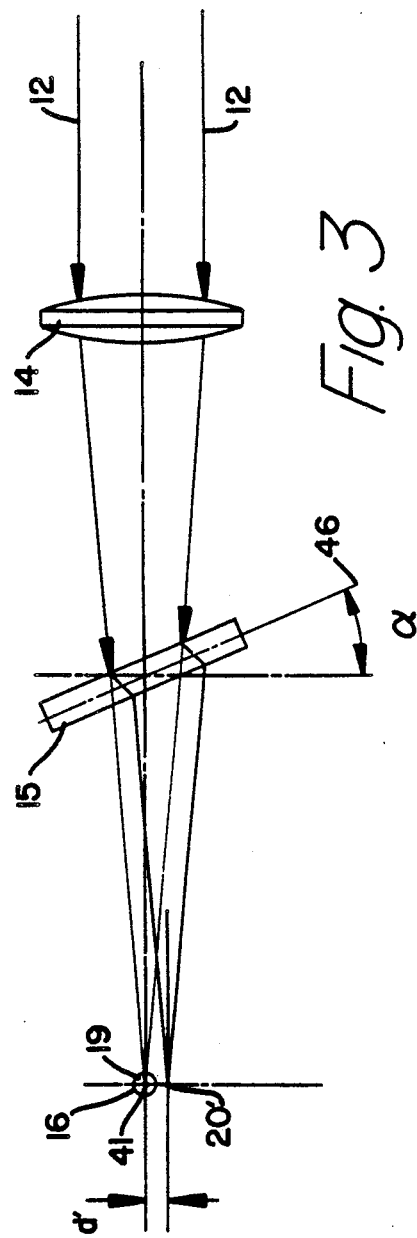

FLOW CYTOMETRY APPARATUS WITH IMPROVED LIGHT BEAM ADJUSTMENT

BACKGROUND OF THE INVENTION

1. Field of the Invention.

The present invention relates to a flow cytometry apparatus, and more particularly, concerns a flow cytometry apparatus for determining one or more characteristics of cells or the like which includes improved optics for the light beam adjustment.

2. Description of the Prior Art.

Flow analysis of particles, such as cells, has been employed in the determination of different characteristics of those particles. Flow cytometry apparatuses have long been utilized for this purpose. In the broadest sense, a flow cytometry apparatus as used and meant herein is an instrument which analyzes cells or particles as they serially flow, substantially one at a time, through a sensing region. Cell volume, size, shape and identification are parameters which are typically determined in a flow cytometry apparatus, particularly as such parameters are related to a source of light directed at the cells when flowing through the sensing region. Light scattered by the flowing cells may be detected at variety of angles with respect to the axis of the incident light beam. Scattered light has served as a function of cell shape, index of refraction, opacity, roughness and the like. Fluorescence emitted by labeled cells which have been excited as a result of passing through the excitation energy of the incident light beam is detectable for identification of specifically labeled cells. Not only is cell analysis performed on the flow cytometry apparatuses, but sorting of cells may also be achieved. In U.S. Pat. No. 3,826,364, a flow cytometry apparatus is disclosed which physically separates particles such as functionally different cell types. In this patented cell sorter, a laser provides illumination which is focused on the stream of particles by a suitable lens or lens system so that there is highly localized scatter from particles therein. In addition, a high intensity source of illumination is directed onto the stream of particles for the excitation of fluorescent particles in the stream. Certain particles in the stream may be selectively charged and then separated by deflecting them into designated receptacles.

When utilizing lasers or other light sources for illumination in flow cytometry apparatuses, obtaining optimum fluorescent pulse height resolution involves a balance between illumination uniformity, which determines the uniformity of fluorescence with particle position, and laser beam intensity, which determines the available fluorescence photon flux. One such technique of improving fluorescence sensitivity in the flow cytometry apparatus is disclosed in U.S. Pat. No. 4,498,766. In the aforementioned patent, fluorescence sensitivity is improved by positioning the focusing lens at an angle relative to the light beam so that the light beam focal waist becomes elongated, and elliptical in nature. The elliptical focal spot allows the light energy from the laser to be focused into a focal spot so that the energy distribution in the direction of particle travel is optimized thereby affecting fluorescence sensitivity. Other light beam focusing devices are described in U.S. Pat. Nos. 4,293,221; 4,243,318 and 3,606,547.

Even though the focused laser or other light beam provides the improvement in fluorescence sensitivity and optimization of the focal spot intensity, optimal performance is minimized if the focused light beam is not properly adjusted on the stream of flowing cells Many flow cytometry apparatuses include one or more devices for adjusting the positioning of the focused light beam on the flowing cells. Conventional positioning methods employ expensive differential micrometers to position the light source itself, or might include optical elements such as mirrors or prisms. Since the biological cells or particles under analysis are typically a few microns in size, the precision of the light beam adjustment is also in the micron range, thus requiring high resolution mechanical displacement devices Simple and inexpensive techniques of adjusting or positioning a focused light beam on the flowing cells are still being sought. The present invention is directed to the discovery of a straightforward mechanism to obtain fine position adjustment of the focused light beam on the cells.

SUMMARY OF THE INVENTION

The flow cytometry apparatus of the present invention for determining one or more characteristics of particles or the like flowing in a liquid stream comprises means for moving particles, substantially one at a time in a liquid flow stream. Means provides a focused beam of light directed toward the particles in the moving stream. Means adjusts the focal point of the light beam on the particles by refracting the light beam to cause a displacement of the focal point. Means for detecting light with respect to each moving particle is included, which also associates the detected light with one or more characteristics of each particle.

In a preferred embodiment of the present invention, the source for providing the beam of light is a laser. A focusing lens is preferably positioned in the optical path of the light beam to focus the light beam on the cells flowing in the flow stream. A light transmissive, substantially flat steering plate is angularly positioned in the optical path between the lens and the flow stream. This steering plate preferably refracts the light beam to cause a lateral displacement of the focal point of the light beam on the stream to thereby obtain an adjustment of the focused light beam. The means for detecting light may include one or more detectors for light scatter, collected at various angles, or fluorescence.

In accordance with the principles of the present invention, improved optics are provided to obtain accurate and fine position adjustment of the focused light beam on the cells flowing in the liquid stream through the flow cytometry apparatus. In the preferred embodiment of the present invention wherein a light transmissive steering plate is included, a relatively straightforward and inexpensive mechanism is available to achieve the position adjustment of the focused light beam. In certain embodiments of the present invention, the steering plate may be adjustable to obtain finer adjustment, or the steering plate may be removable in the event that replacement is needed or a variation on the adjustment is required. The effect of the steering plate of the present invention is to cause a displacement of the focused light beam on the stream of flowing cells. As a result of this displacement, the focal point of the light beam is adjusted so that optimum fluorescence pulse height resolution is obtainable. Once the steering plate is properly set, the displacement of the light beam is substantially invariant with lateral motions of the steering plate produced by thermal expansions or locking devices. The present invention thus permits optical adjustments that are easy to make and result in high stability of performance.

BRIEF DESCRIPTION OF THE DRAWINGS

FIG. 1 is a schematic illustration of a preferred embodiment of the optical elements and light paths of a flow cytometry apparatus of the present invention for determining one or more characteristics of cells or the like;

FIG. 2 is an enlarged schematic representation of the light beam and the preferred beam steering member of the present invention illustrated from a side view; and FIG. 3 is an enlarged schematic representation of the light beam and an alternate orientation of the preferred steering member of the present invention as illustrated in a top view.

DETAILED DESCRIPTION

Figure 1:
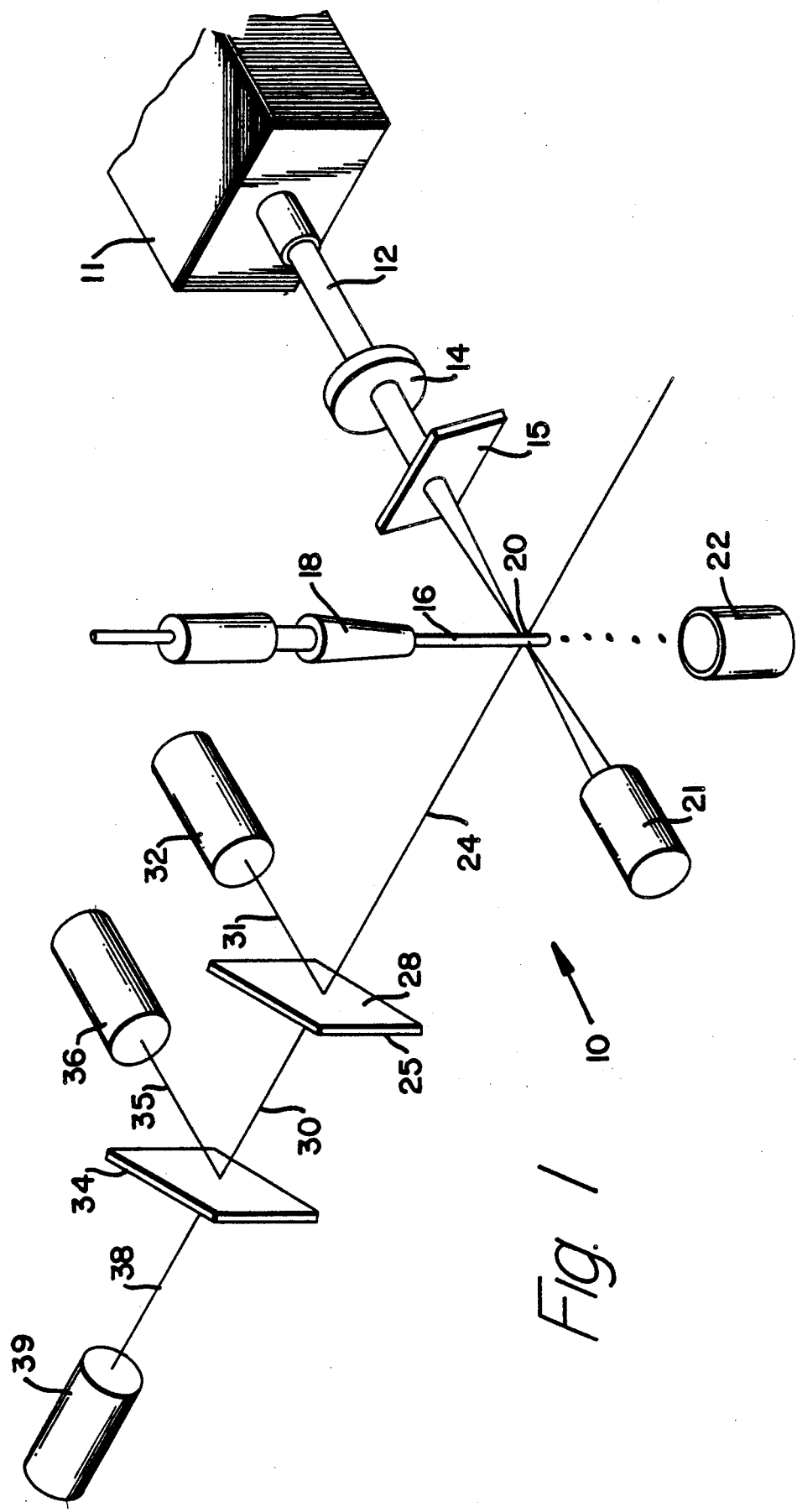

While this invention is satisfied by embodiments in many different forms, there is shown in the drawings and will herein be described in detail preferred embodiments of the invention, with the understanding that the present disclosure is to be considered as exemplary of the principles of the invention and is not intended to limit the invention to the embodiments illustrated. The scope of the invention will be measured by the appended claims and their equivalents.

Referring to the drawings, and FIG. 1 in particular, the optical and particle flow elements of a flow cytometry apparatus 10 are illustrated. The optical and flow elements of FIG. 1 represent the major components of a flow cytometry apparatus for moving particles, such as cells or the like, in a liquid stream, substantially one at a time, in order to assess those particles for specific characteristics thereof. For example, the elements of the apparatus of FIG. 1 may be included in a FAC TM fluorescence-activated cell sorter, manufactured and sold by Becton Dickinson Immunocytometry Systems, Mountain View, Calif. The FACS cell sorter analyzes and sorts cell populations on the basis of light scatter and fluorescence in a wide variety of research laboratory applications. In addition to the optical and flow elements to be described in more particular detail herein, and which may be embodied in an instrument such as the FACS cell sorter, other details of a cell sorting apparatus useful in conjunction with the present invention are described in U.S. Pat. No. 3,826,364. It is understood that the present invention is useful in many different types of flow cytometry apparatuses whether measuring light scatter, fluorescence, particle volume or other optical parameters for the identification or quantification of cells or the like in a sample liquid medium. The optical elements, in particular, of the present invention represent the essence of the improvement in flow cytometry apparatuses such as described in the aforementioned patent.

As illustrated in FIG. 1, light energy is provided for the present flow cytometry apparatus by a light source 11 such as a laser which provides a collimated beam of light at a singular wavelength, or an arc lamp, such as a mercury or xenon arc lamp, which provides an incoherent or non-collimated beam of light comprising a broad spectrum of wavelengths.

Excitation energy is provided in flow cytometry apparatus 10 by a beam of light 12 produced by light source 11. Typically, the beam of light passes through a focusing lens 14 positioned in the optical path of the light beam. Lens 14 focuses the light beam at a liquid stream 16 containing the particles or cells under investigation. In the present invention, however, a light transmissive steering member or plate 15 is positioned in the optical path between lens 14 and liquid flow stream 16 to obtain an adjustment of the focused light beam on the liquid stream. The details of the adjustment of the focused light beam will be described in more detail hereinafter in conjunction with FIGS. 2 and 3.

As seen in FIG. 1, a nozzle 18, incorporated within the flow cytometry apparatus of the present invention, facilitates the flowing of cells or particles within liquid stream 16. The utilization of a nozzle of this type is well-known and is described, for example, in U.S. Pat. No. 3,826,364. Nozzle 18 provides a hydrodynamically focused flow of cells within a sheath fluid, the sheath fluid and cells comprising liquid flow stream 16. As each cell or particle passes through the adjusted focused light region 20, where light beam 12 intersects liquid stream 16, light scattered thereby may be detected. An appropriate photodetector 21 is positioned to receive light scattered forwardly by each cell.

Fluorescence, if emitted by cells energized by the illumination from the light source, may also be detected. Similarly, light scattered in different directions, besides the forward direction, may be detected. In laser-excited flow cytometry, both fluorescence and wide angle light scatter are typically collected at an angle whose viewing axis is 90° relative to the excitation axis of light beam 12. In FIG. 1, axis 24 represents the 90° viewing axis for the collection of fluorescence and wide angle scatter.

In order to collect fluorescence and light scatter at the 90° angle from the incident light beam, the light scatter and fluorescence is typically separated or split. This separation may be accomplished by many different techniques such as a dichroic filter or beam splitter 25. In the embodiment being described, 90° light scatter is reflected off leading face 28 of beam splitter 25, and travels along axis 31 so that it may be collected in photodetector 32. On the other hand, fluorescence is transmitted through beam splitter 25 and travels along axis 30. The fluorescence traveling along axis 30 may be further refined or separated by the provision of a dichroic mirror 34. This mirror may be utilized to separate the different color wavelengths in the fluorescence signal. Thus, and for example, fluorescence in the green color region may be reflected by dichroic mirror 34 along axis 35 and collected in an appropriate photodetector 36. Fluorescence in the red color region, for example, may be transmitted through dichroic mirror 34 along axis 38 and collected in an appropriate photodetector 39. While not illustrated in FIG. 1, those skilled in the art will appreciate that various lens, filters, barriers or the like may be employed in conjunction with each of the photodetectors to obtain as pure a signal as possible. Obtaining such optically clean signals is most desirable particularly when a four-parameter sensing apparatus (two fluorescence channels and two light scatter channels) is utilized, such as the apparatus illustrated in FIG. 1.

Before describing the beam steering member of the present invention, it should be pointed out that the particles in liquid stream 16 may be collected in an appropriate container 22, or, perhaps, may be sorted and collected in different containers if the flow cytometry apparatus employs a sorting capability.

Turning now to FIG. 2, the details of the light beam adjustment feature of the present invention are more clearly illustrated. It can be seen that light beam 12 passes through focusing lens 14, which may be a singular lens or an assembly of lenses, depending upon design requirements It is the purpose of lens 14 to focus the light at sensing region 19 which represents the intersection of light beam 12 and liquid flow stream 16. The axis of liquid flow stream is designated by numeral 41 But for the presence of steering plate 15, light beam 12 would be focused at focal region 19.

Inclusion of steering plate 15, as illustrated in FIG. 2, provides a fine position adjustment of the focused light beam by causing a displacement of the focal region in a substantially vertical direction. To achieve the displacement of the focal region, light transmissive steering plate 15 is positioned at an angle in the light path. Specifically, axis 42 represents an axis which is substantially parallel to axis 41 of liquid flow stream 16. Steering plate 15 is positioned at axis 42 and is angularly oriented so that its axis 44 forms an angle $\theta$ therewith. Once light beam 12 strikes the light transmissive steering plate, the light beam is refracted to cause a displacement of the focal point, in this instance, in a downward vertical direction to adjusted light region 20. The displacement between original focal region 19 and adjusted focal region 20 is designated by letter "d" in FIG. 2. Displacement "d" is governed by the equation:

$$d = t \frac{\sin(\theta - \beta)}{\cos \beta}$$

where,
$t$ = thickness of plate 15

$$\beta = \sin^{-1}\left[\frac{N_1}{N_2} \sin \theta\right]$$

$N_1$ = refractive index of medium surrounding plate 15 = 1.00 for air
$N_2$ = refractive index of plate 15

This small displacement of the focal region permits very fine position adjustment of the focused light beam on the cells or particles flowing in the liquid stream. Further, the adjusted focal region allows improved sensitivity and efficiency in obtaining light signals, particularly fluorescence.

Adjustment of the focused light beam is not restricted to vertical displacement of the focal region. In FIG. 3, horizontal displacement of the focal point of the light beam is illustrated. In this alternative approach, steering plate 15 is positioned at an axis 45 which is substantially perpendicular to axis 41 of flow stream 16. Further, steering plate 15 has its axis 46 angularly oriented at an angle $\alpha$ with respect to axis 45. Accordingly, light beam 12 which strikes light transmissive steering plate 15 is refracted to cause a displacement of the focal region from point 19 to point 20'. The horizontal displacement is designated by letter "d'". Thus, fine position adjustment of the focused light beam may be achieved by displacing the focal region of the light beam in a horizontal, as well as a vertical direction with respect to the flow stream It is appreciated and understood that displacement of the focal region to provide fine adjustment may have both vertical and horizontal components depending upon the angular orientation of steering plate 15. Similar displacement of the focal region may be produced by locating steering plate 15 between light source 11 and focal lens 14.

Other features may also be included in the present flow cytometry apparatus to improve light beam adjustment. For instance, lens 14 may be adjustably positioned in the flow cytometry apparatus so that the focusing of the light beam toward the flow stream may be varied for optimization purposes. Similarly, steering plate 15 may be adjustably mounted in the flow cytometry apparatus so that fine adjustments of the focused light beam may be conveniently made. Interchangeable steering plates may also be provided so that one such steering plate may be removed and replaced depending upon design of the flow cytometry apparatus and the particular use at hand.

Steering plate 15 is preferably a substantially flat, thin piece of glass. This material is inexpensive, and when used as a steering member as contemplated by the present invention, provides a simple and straightforward mechanism for adjusting the focused light beam on the cells in the flow stream. While other light transmissive materials may be utilized for the steering plate, glass is the most desirable. Moreover, best results have been achieved when using glass having an index of refraction between 1.50 and 1.55, and a thickness between 0.25 and 1.00 mm. These indices of refraction and thicknesses are merely exemplary of some features of the steering plate, and are not meant to be limitative of the present invention. It is appreciated that plate 15 need not be planar for purposes of the present invention. For example, if light beam 12 is collimated and plate 15 is located between light source 11 and focal lens 14 no displacement results unless plate 15 has a wedge shape, i.e., like a prism. While the angle of displacement of the steering plate with respect to the aforementioned axes may vary according to different factors, including the amount of focal region displacement, typical angular displacement for purposes of the present invention may range between +30° and −30°.

Once the above-described photodetectors receive the various light signals, the information gained thereby may be further utilized. The various photodetectors may be well-known photomultiplier tubes or similar devices which convert light signals into electrical impulses so that the light thereby detected may be associated with the cells flowing through the apparatus. The electrical signals from the photodetectors are typically fed to the electronics (not shown) of the apparatus for purposes of display, storage or further processing so that one or more characteristics of the cells under analysis may be determined.

Thus, the present invention provides improved light beam adjustment in a flow cytometry apparatus. By including a steering plate in the focused light path, a straightforward and inexpensive technique is offered for fine position adjustment of the focused light beam.

What is claimed is:

1. A flow cytometry apparatus for determining characteristics of cells flowing in a liquid stream comprising:
   means for moving cells, substantially one at a time, in a liquid flow stream;
   a light source for providing a beam of illumination directed at the cells in said flow stream;
   a focusing lens positioned in the optical path of said light beam to focus said light beam on said cells flowing in the flow stream;
   a light beam steering member angularly positioned in the optical path between said lens and said flow stream for refracting the focused light beam to cause a displacement of the focal point of said beam on said stream, said steering member being a light transmissive plate to thereby obtain an adjustment of said focused light beam;

means for detecting light associated with each moving cell as said cell passes through said adjusted, focused light beam; and means for using said detected light to determine one or more characteristics of said cells.

2. The apparatus of claim 1 wherein said plate is substantially flat and has a thickness between 0.25 and 1.00 mm.

3. The apparatus of claim 1 wherein said plate has a refractive index between 1.50 and 1.55.

4. The apparatus of claim 3 wherein said plate is made of glass.

5. A flow cytometry apparatus for determining characteristics of cells flowing in a liquid stream comprising:

means for moving cells, substantially one at a time, in a liquid flow stream;

laser for providing an incident beam of illumination directed at the cells in said flow stream;

a focusing lens positioned in the optical path of said light beam to focus said light beam on said cells flowing in the flow stream;

a light transmissive, substantially flat steering plate angularly positioned in the optical path between said lens and said flow stream for refracting the focused light beam to cause a displacement of the focal point of said light beam on said stream to thereby obtain an adjustment of said focused light beam;

means for detecting light associated with each moving cell as said cell passes through said adjusted, focused light beam; and means for using said detected light to determine one or more characteristics of said cells.

* * * * *